(12) United States Patent
Monahan et al.

(10) Patent No.: US 7,476,401 B2
(45) Date of Patent: Jan. 13, 2009

(54) PROTEIN AND PEPTIDE DELIVERY TO MAMMALIAN CELLS IN VITRO

(75) Inventors: Sean D. Monahan, Madison, WI (US); Vladimir G. Budker, Middleton, WI (US); Kirk Ekena, Middleton, WI (US); Lisa Nader, Madison, WI (US)

(73) Assignee: Mirus Bio LLC, Madison, WI (US)

(*) Notice: Subject to any disclaimer, the term of this patent is extended or adjusted under 35 U.S.C. 154(b) by 76 days.

(21) Appl. No.: 11/248,993

(22) Filed: Oct. 12, 2005

(65) Prior Publication Data

US 2006/0034909 A1    Feb. 16, 2006

Related U.S. Application Data

(62) Division of application No. 10/767,329, filed on Jan. 29, 2004.

(60) Provisional application No. 60/443,645, filed on Jan. 30, 2003.

(51) Int. Cl.
*A61K 9/127* (2006.01)
*A61K 48/00* (2006.01)
*C12N 15/88* (2006.01)

(52) U.S. Cl. ............... 424/450; 435/455; 435/458

(58) Field of Classification Search .................. None
See application file for complete search history.

(56) References Cited

U.S. PATENT DOCUMENTS 3,726,972 A * 4/1973 Miller .................... 514/21
4,859,538 A * 8/1989 Ribi ..................... 428/474.4
6,673,612 B2 * 1/2004 Monahan et al. ......... 435/458
6,818,626 B1 * 11/2004 Wolff et al. .............. 514/44
6,919,091 B2 * 7/2005 Trubetskoy et al. ........ 424/450
2003/0054007 A1 * 3/2003 Felgner et al. ........... 424/178.1
2003/0235916 A1 * 12/2003 Monahan et al. .......... 435/455

FOREIGN PATENT DOCUMENTS

EP         0335133         *  6/1989

OTHER PUBLICATIONS

Zelphati et al., "Intracellular Delivery of Proteins with a New Lipid-Mediated Delivery System," 2001, JBC, vol. 276, No. 37 pp. 35103-35110.*
Maa et al., "Biopharmaceutical Powders: Particle Formation and Formulation Considerations," 2000, Current Pharmaceutical Biotechnology, 1, pp. 283-302.*
Blattler et al., "New Heterobifunctional Protein Cross-Linking Reagent That Forms and Acid Liabile Link", Biochemistry 1985, 24, pp. 1517-1524.*
Hermanson et al., "Bioconjugate Techniques" San Diego, Academic Press, 1996.*
Chatzinikolaidou, M.; Laub, M.; Rumpf, H.; Jennissen, H.P. "Biocoating of Electropolished and Ultra-hydrophilic Titanium and Cobalt Chromium Molybdenum Alloy Surfaces with Proteins", Mat.-Wiss. u. Werkstofftech, 33 (12) p. 720-727 (Dec. 2002).*
Lipshutz, Bruce H; Shin, Young-Jun. "A new silyl linker for reverse-direction solid-phase peptide synthesis", Tetrahedron Letters 42 (2001) p. 5629-5633.*

* cited by examiner

*Primary Examiner*—M P Woodward
*Assistant Examiner*—Bethany Barham
(74) *Attorney, Agent, or Firm*—Mark K Johnson; Kirk Ekena

(57) ABSTRACT

Compositions and methods for delivery of proteins and peptides to mammalian cells in vitro are described. Specifically, polypeptide-surfactant complexes formed from noncovalent hydrophobation of polypeptides and reversible hydrophobic modification of polypeptides are described. The compositions can be used to delivery positively charged, negatively charged and charge neutral polypeptides to cells.

7 Claims, 3 Drawing Sheets

Protein Delivery to Mammalian Cells

PROTEIN AND PEPTIDE DELIVERY TO MAMMALIAN CELLS IN VITRO

CROSS-REFERENCE TO RELATED APPLICATIONS

This application is a divisional of application Ser. No. 10/767,329 filed Jan. 29, 2004, pending, which claims priority from Application No. 60/443,645 filed on Jan. 30, 2003.

FIELD OF INVENTION

The present invention relates to methods and formulations for the delivery of peptides and proteins to cells.

BACKGROUND OF THE INVENTION

Recent advances in the areas of medicine and biotechnology have led to the increased isolation and development of biologically active and therapeutically or diagnostically useful peptides and proteins. However, peptides and proteins generally have limited stability (half-life) physiologically, and are rapidly degraded. Additionally, peptides and proteins can have difficulty in efficiently interacting with or crossing cell membranes. Peptides and proteins are generally comprised of both charged and uncharged amino acid residues that impart structure and solubility to the peptide or protein. However, this charge can hinder membrane binding and membrane transport in cells. Therefore the development of methods for delivering peptides and proteins to cells is a current and continuing need in the areas of research and therapeutics.

Hydrophobic modification of compounds is known to increase binding of the compound to the cellular membranes. Recently, several examples of hydrophobic modification of peptides and proteins have been described in the literature (Storch et al. 1996; Kamyshny et al. 1997; Wang et al. 1997; Wang et al. 1999; Schreier et al. 2000; Wang et al. 2000; Wang et al. 2002; Wang et al. 2003). Hydrophobic modification entails the covalent attachment of one or more hydrophobic substituents to the polypeptide, usually through a nitrogen atom on the polypeptide. This modification can be accomplished through the use of chemically stable or chemically labile groups. If the attachment group is chemically labile, the bond can cleave at a certain rate under physiological conditions in order to allow the hydrophobic substituents to separate from the polypeptide. Following delivery of the hydrophobized polypeptide, several internalization pathways are possible. For example the complex can bind to the cellular membrane and either be endocytosed, directly transverse the membrane, or be trapped in or on the membrane. The complex can also be endocytosed and then cross internal membranes. In addition to the previously mentioned possibilities, if the hydrophobic group is labile, the hydrophobic group may cleave from the polypeptide in or near the cell. The polypeptide can then enter the cell via the mechanisms that are possible for the internalization of an unmodified polypeptide.

Several compound classes have been shown to be effective linkers for the hydrophobation, including simple acylation. Acylation with fatty acids or a variety of cyclic anhydrides are examples. Cyclic anhydrides have been shown a great deal of interest due to the ability of the linkage following the modification of the polypeptide. For example, maleic anhydrides have been previously utilized for reversible amine modification. The resulting maleamic acids are known to be stable under basic conditions, but hydrolyze rapidly under acidic conditions. Hydrophobic modification has even shown promise for the oral delivery of protein complexes. For example, Wang et al. has described the oral delivery of salmon calcitonin through the use of a reversible hydrophobation of the protein (Wang et al. 2003).

In addition to hydrophobation, several additional methods have been developed for the delivery of polypeptides to cells. Liposomal and micellar delivery, polymer conjugates, and systems involving combinations of polymers and lipids have all been used for the delivery of polypeptides to cells (Trubetskoy et al. 1993; Bijsterbosch et al. 1994; Rao et al. 1997; Yoshikawa et al. 1997; Capan et al. 1999; Schibli et al. 1999a; Schibli et al. 1999b; Montserret et al. 2000; Rao et al. 2000; Betz et al. 2001; Futaki et al. 2001; Gupta et al. 2001; Kisel et al. 2001; Nagy et al. 2001; Wang et al. 2001; Zelphati et al. 2001; Caliceti, et al. 2003; Copland et al. 2003; Mahato et al. 2003; Tiyaboonchai et al. 2003; Yang et al. 2003). Currently, there are several kits available from a variety of manufactures for the delivery of polypeptides to cell in vitro based on cationic lipids. However, the liposomal delivery of polypeptides has not been shown to be general. Since charge is the controlling factor in the binding of the peptide with the lipid, widely variable results would be expected based on the charge of the peptide. In the molecular conjugate area, several examples of increased serum half lives have been demonstrated following conjugations with a polymer. In all of these areas, there is a great deal of examples in which the lipid/liposome, micelle, and polymer conjugates are targeted to a cell utilizing some type of polypeptide acting as a targeting ligand.

SUMMARY OF THE INVENTION

In a preferred embodiment, we describe methods for delivery of proteins (positively charged, negatively charged and charge neutral) and peptides (negatively charged, positively charged and charge neutral) into mammalian cells in vitro. The techniques involve noncovalent hydrophobation and reversible hydrophobic modification.

The present invention relates to new methods and formulations for the delivery of polypeptides to cells. In a preferred embodiment, the present invention encompasses the noncovalent interaction of a charged polypeptide with a surfactant of opposite charge to form a polypeptide-surfactant mixture. The polypeptide-surfactant mixture is then dried to form a dried salt complex. Forming a dried salt complex comprises: lyophilizing the polypeptide-surfactant mixture. The dried salt complex is then dissolved in an appropriate organic solvent or in an organic/aqueous solvent mixture. The resultant complexes are then contacted with the cell for delivery of the polypeptide to a cell.

In a preferred embodiment of the invention, the dried salt complex is dissolved in an appropriate organic solvent or in an organic/aqueous solvent mixture, and mixed with lipids or liposomes. In this embodiment, the lipid(s) and liposomes can posses additional functionality, for example, membrane active compounds, cell penetrating compounds, cell targeting signals, interaction modifiers, steric stabilizers. Additionally, the lipid(s) and liposomes can posses reactive groups to which membrane active compounds, cell penetrating compounds, cell targeting signals, interaction modifiers, steric stabilizers can be attached. The mixture is then applied to cells.

In another preferred embodiment of the invention, the dried salt complex is dissolved in an appropriate organic solvent or in an organic/aqueous solvent mixture, mixed with lipid(s), and dried to a film. The resulting film is hydrated with an aqueous solution, vortexed, bath sonicated, and then applied to cells. In this embodiment, the lipid(s) and liposomes can posses additional functionality, for example, membrane active compounds, cell penetrating compounds, cell targeting signals, interaction modifiers, steric stabilizers. Additionally, the lipid(s) and liposomes can posses reactive groups to which membrane active compounds, cell penetrating compounds, cell targeting signals, interaction modifiers, steric stabilizers can be attached.

In a preferred embodiment we describe the reversible modification of ammonium salts, such as in amine containing polypeptides, with compounds of general formula I

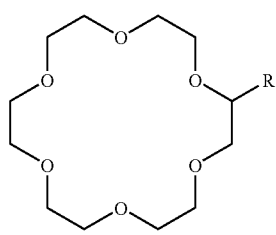

wherein R is an alkyl group. Compounds of this structure are able to chelate amines on a polypeptide. Additional substituents can be present on any carbon atom of the system as long as the crown ether retains the ability to chelate to an amine. Additional substituents include steric groups, targeting groups, and polymers. The invention is also meant to encompass the delivery to cells of the modified polypeptide by mixing the complex with lipid(s) or by hydrating the lipid(s) with a solution containing the modified polypeptide. The lipid(s) can posses additional functionality, for example, membrane active compounds, cell penetrating compounds, cell targeting signals, interaction modifiers, steric stabilizers. Additionally, the lipid(s) can posses reactive groups to which membrane active compounds, cell penetrating compounds, cell targeting signals, interaction modifiers, steric stabilizers can be attached.

In yet another aspect, the present invention encompasses the reversible modification of ammonium salts, such as in amine containing polypeptides, with compounds of general formula II

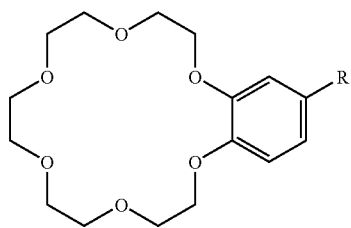

wherein R is an alkyl group. Compounds of this structure are able to chelate amines on a polypeptide. Additional substituents can be present on any carbon atom of the system as long as the crown ether retains the ability to chelate to an amine. Additional substituents include steric groups, targeting groups, and polymers. The invention is also meant to encompass the delivery to cells of the modified polypeptide by mixing the complex with lipid(s) or by hydrating the lipid(s) with a solution containing the modified polypeptide. The lipid(s) can posses additional functionality, for example, membrane active compounds, cell penetrating compounds, cell targeting signals, interaction modifiers, steric stabilizers. Additionally, the lipid(s) can posses reactive groups to which membrane active compounds, cell penetrating compounds, cell targeting signals, interaction modifiers, steric stabilizers can be attached.

In a preferred embodiment, the present invention encompasses the reversible modification of polypeptides with compounds of general formula III

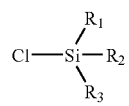

wherein $R_2$, $R_2$, and $R_3$ are independent and are selected from the group consisting of halogen, alkyl, or aryl. The invention is meant to encompass the delivery to cells of the modified polypeptide by mixing the complex with lipid(s) or by hydrating the lipid(s) with a solution containing the modified polypeptide. The lipid(s) can posses additional functionality, for example, membrane active compounds, cell penetrating compounds, cell targeting signals, interaction modifiers, steric stabilizers. Additionally, the lipid(s) can posses reactive groups to which membrane active compounds, cell penetrating compounds, cell targeting signals, interaction modifiers, steric stabilizers can be attached.

In a preferred embodiment, the present invention encompasses the reversible modification of polypeptides with compounds of general formula IV

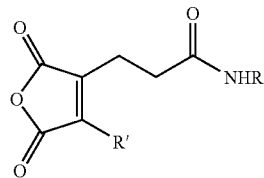

in which R is selected from the group consisting of alkyl, aryl, aralkyl, a steric group, or a targeting group, and R' is selected from the group of hydrogen, alkyl, or aryl. The invention is meant to encompass the delivery to cells of the modified polypeptide, by mixing the complex with lipid(s) or by hydrating the lipid(s) with a solution containing the modified polypeptide. The lipid(s) can posses additional functionality, for example, membrane active compounds, cell penetrating compounds, cell targeting signals, interaction modifiers, steric stabilizers. Additionally, the lipid(s) can posses reactive groups to which membrane active compounds, cell penetrating compounds, cell targeting signals, interaction modifiers, steric stabilizers can be attached.

DETAILED DESCRIPTION OF THE INVENTION

Figure 1:
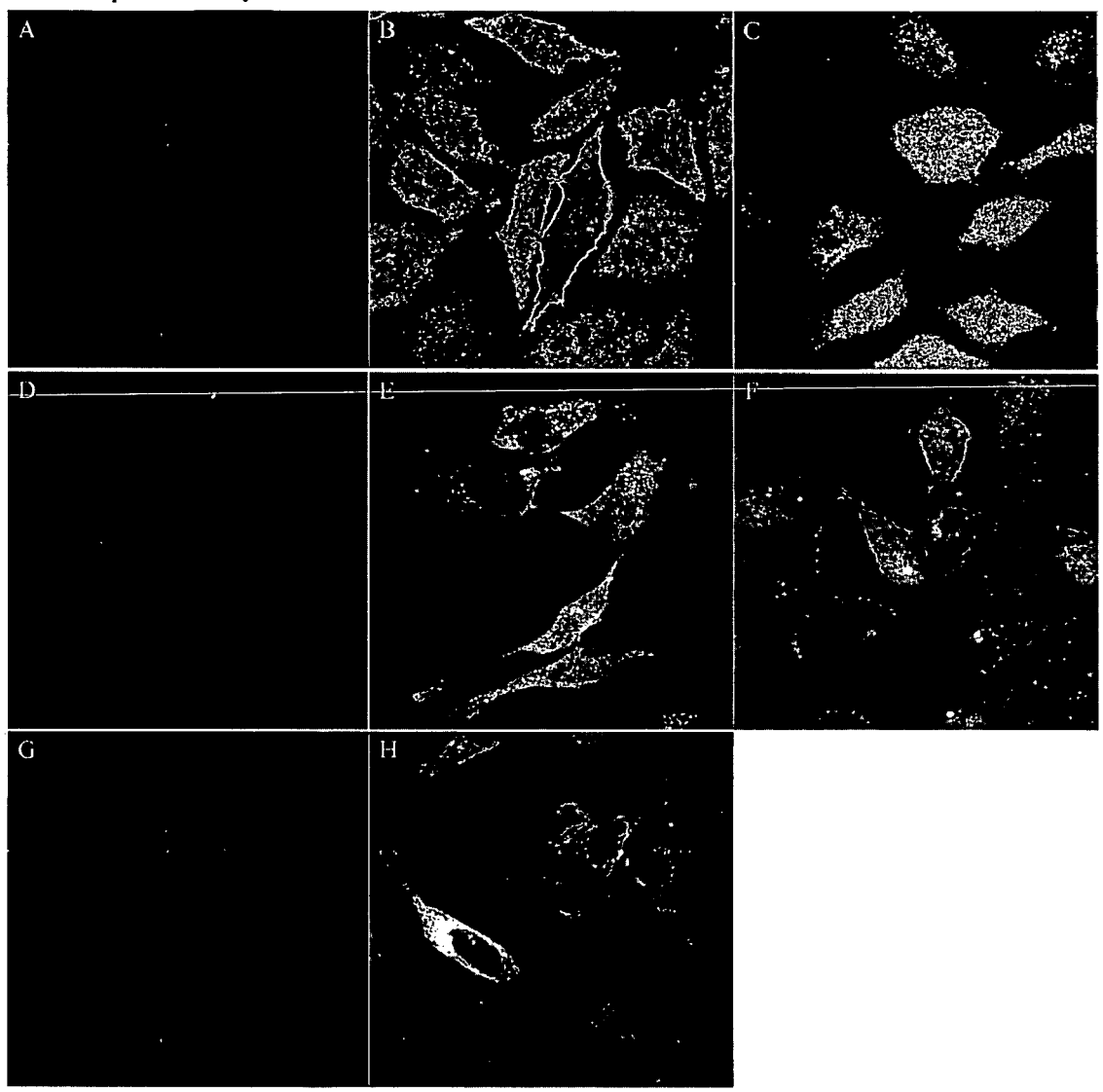
FIG. 1. Peptide delivery to mammalian cells. (A) NES peptide control, 2 μg NES peptide incubated with HeLa cells according to technique #1. (B) formulation #56, technique #1. (C) modification #8, formulation #30, technique #1. (D) PosPep control, 2 μg PosPep incubated with HeLa cells according to technique #1. (E) formulation #57, technique #1. (F) modification #10, formulation #12, technique #1. (G) NePep control, 2 μg NegPep peptide incubated with HeLa cells according to technique #2. (H) formulation #2, technique #2. Formulations are described in example 4, techniques are described in example 6.

In the present invention, we describe methods for delivery of proteins (positively charged, negatively charged and charge neutral) and peptides (negatively charged, positively charged or charge neutral) into mammalian cells in vitro. Noncovalent hydrophobation and reversible hydrophobic modification of polypeptide are described. In addition novel compounds are described which can by used for the hydrophobation of polypeptides.

It is known in the literature that hydrophobation (also referred to as lipidation) of compounds and macromolecular carrier systems can increase cellular interactions (Storch et al. 1996; Kamyshny et al. 1997; Wang et al. 1997; Wang et al. 1999; Schreier et al. 2000; Wang et al. 2000; Wang et al. 2002; Wang et al. 2003). The present invention describes methods for the noncovalent hydrophobation of polypeptides. For the intent of this description, polypeptide encompasses the terms peptide and protein. Additionally, the invention details systems for the reversible hydrophobic modification of polypeptides. By adjusting the molar ratio of reagents utilized in the hydrophobic modification (both for the noncovalent hydrophobation and for the reversible modification), the methods provide for tailoring the hydrophobation level of polypeptide in order to optimize cellular delivery.

In one embodiment, the formation of a dried salt complex is described. The dried salt complex can be formed from through lyophilization of a polypeptide-surfactant complex or polypeptide-surfactant mixture. This dried salt complex is soluble in organic solvents or in mixed organic/aqueous solvents. A polypeptide-surfactant complex is the complex obtained from mixing a polypeptide with a surfactant of opposite charge. The polypeptide can be as the free acid or base or as the acid or base addition salt. If the polypeptide is the acid or base addition salt, then the surfactant employed for the complex formation should be the corresponding acid or base addition salt. If the polypeptide is the free acid or base, then the surfactant employed for the complex formation should be the corresponding free acid or base. The polypeptide-surfactant complex can be between one or more charged groups on a polypeptide with one or more surfactant molecules of opposite charge.

The polypeptide-surfactant complex can be prepared for example, from the positively charged amine groups on a polypeptide when interacted with a negatively charged surfactant. Conversely, a polypeptide-surfactant complex can be prepared from the negatively charged carboxylate groups on a polypeptide when interacted with a positively charged-surfactant. A cationic polypeptide is a polypeptide containing a net positive charge. The polypeptide can contain units that are charge positive, charge neutral, or charge negative, however, the net charge of the polypeptide must be positive. An anionic polypeptide is a polypeptide containing a net negative charge. The polypeptide can contain units that are charge negative, charge neutral, or charge positive, however, the net charge on the polypeptide must be negative. A neutral polypeptide is a polypeptide containing a net neutral charge. The polypeptide can contain units that are charge negative, charge neutral, or charge positive, however, the net charge on the polypeptide must be negative. The term zwitterionic refers to the product (salt) of the reaction between an acidic group and a basic group that are part of the same molecule.

For positively charged polypeptides, the polypeptide-surfactant complex can, in principle, be prepared from any surfactant in which the pKa of the surfactant is lower than the pKa of the amine groups on the polypeptide. Examples of negatively charged surfactants include carboxylic acid containing surfactants (or pharmaceutically acceptable salts of carboxylic acids), phosphoric acid containing surfactants (or pharmaceutically acceptable salts of phosphoric acids, i.e. phosphates), and sulfuric acid containing surfactants (or pharmaceutically acceptable salts of sulfuric acids, i.e. sulfates). For example, oleic acid, oleic acid sodium salt, palmitic acid and its salts, pamitoleic acid and its salts, and sodium dodecylsulfate.

The polypeptide-surfactant complex can also be prepared from the negatively charged groups on a polypeptide (carboxylic acid, phosphates, or sulfates) interacting with a positively charged surfactant. In principle, the polypeptide-surfactant complex can be prepared from any surfactant in which the pKa of the surfactant is higher than the pKa of the acidic group(s) on the polypeptide. For example, a negatively charged polypeptide can be interacted with cetyltrimethylammonium bromide in order to complex the negatively charged groups of a polypeptide. Examples of positively charged surfactants include, but are not limited to cetyltrimethyl-ammonium bromide, cetylpyridinium bromide, dodecylpyridinium chloride, dodecyltrimethylammonium bromide, and cetyldimethylethylammonium bromide.

A surfactant refers to a compound that contains a polar group (hydrophilic) and a non-polar (hydrophobic) group on the same molecule. The hydrophobic group of the surfactant is most preferably an alkyl chain of 4 to 30 carbon atoms, and can contain sites of unsaturation. A variety of methods other than those described here can be envisioned for preparing the polypeptide-surfactant complex, and for drying the complex to afford the dried salt complex and are meant to be included within the scope of this invention.

Another embodiment of the present invention involves the association of the dried salt complex with one or more lipids. By association in this case we mean that the dried salt complex is mixed with the lipid or with liposomes. For example, the dried salt complex can be dissolved in an organic solution and added to an organic solution containing lipid(s). The resulting mixture can be dried to a film as is typically done in the art with liposomal preparations, and hydrated with an aqueous solution to generate the liposomes. Alternatively, the dried salt complex can be dissolved in an organic solution (for example ethanol) and added to lipid(s) in an organic solution (for example ethanol). The resulting solution can be utilized directly for liposomal formation as is typically done in the art for liposomal preparations. Alternatively, the dried salt complex can be dissolved in an organic solution or organic/aqueous solution mixture and added to a lipid film to rehydrate the film or added directly to liposomes.

Another aspect of the present invention encompasses the formation of a polypeptide-surfactant complexes by the interaction of the polypeptide with a surfactant-chelator. In the present invention, a crown ether chelator possessing a hydrophobic group is complexed with the ammonium salt of a polypeptide in order to associate a hydrophobic group with the polypeptide. Crown ethers, and more specifically 18-crown-6 ethers, are known to chelate to ammonium salts (Greene et al. 1999). Inclusion of a hydrophobic group off of the crown ether, as in general formula I and II, allows for a noncovalent association of the hydrophobic group to a polypeptide amine group. In the present invention the alkyl groups in general formula I are preferably from 3-30 carbons in length, can contain unsaturated carbons, and can be branched. In the present invention the alkyl groups in general formula II are preferably from 3-30,carbons in length, can contain unsaturated carbons, amide groups, and esters, and can include branching. The association of the hydrophobic group to the polypeptide is transient since the ammonium salt can be displaced from the crown ether. The formed polypeptide-surfactant complex can be dried to afford a dried salt complex. However, for polypeptide-surfactant complexes formed using chelators of general formula I or II, the invention is not limited to the dried salt complex. Additional groups can be present on any carbon atom of the chelators of general formula I and II, so long as the crown ether can still chelate to the ammonium salt. Other groups include for example, membrane active compounds, cell penetrating compounds, cell targeting signals, interaction modifiers, steric stabilizers. Additionally, the chelator can posses reactive groups to which membrane active compounds, cell penetrating compounds, cell targeting signals, interaction modifiers, steric stabilizers can be attached.

A polypeptide-surfactant complex formed from general formula I and II can further be formulated or associated with lipids or liposomes. By association in this case we mean that polypeptide-surfactant complex formed from general formula I and II is mixed with the lipid or with liposomes. For example, the polypeptide-surfactant complex formed from general formula I and II can be added to an organic solution containing lipid(s). The resulting mixture can be dried to a film and hydrated with an aqueous solution to afford the liposomes. Alternatively, a polypeptide-surfactant complex formed from general formula I and II can be added to a lipid film to rehydrate the film, or can be added directly to liposomes. The lipid(s) and liposomes can posses additional functionality selected from the list consisting of: membrane active compounds, cell penetrating compounds, cell targeting signals, interaction modifiers, steric stabilizers. Additionally, the lipid(s) and liposomes can posses reactive groups to which such groups can be attached.

The present invention also involves systems for the reversible hydrophobic modification of polypeptides in order to broaden or enhance their ability to be delivered to cells through a variety of formulations. As outlined, the hydrophobic modification can increase the ability to formulate the polypeptide in a form for delivery to a cell. However, the reversibility is an important aspect of the experiment in that the hydrophobic modification is able to separate from the polypeptide under physiological conditions, thus allowing the natural (unmodified) polypeptide to be regenerated. Two systems are described for use in the reversible modification of polypeptides.

As such, in one aspect of the invention, the invention encompasses the reversible hydrophobic modification of polypeptides by alkyl chlorosilanes to form the reversible hydrophobic polypeptide complex. Silylchlorides are known to react with a wide variety of organic functional groups (Greene et al. 1999) to afford silylated derivatives. The reaction of an amine and a silylchloride generates a silazane. Silazanes are generally very hydrolytically labile, making them useful as temporary hydrophobation systems. Upon hydrolysis, the original amine is regenerated together with a silanol or silyl ether. The present invention encompasses the modification of polypeptides with silyl chlorides of general formula III

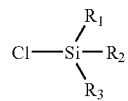

wherein $R_1$, $R_2$, and $R_3$ are independent and are selected from the group consisting of halogen, alkyl, or aryl. More specifically, $R_1$, $R_2$, and $R_3$ are independent and are selected from the group consisting of halogen (chloride or bromide), alkyl (from 1-30 carbons, can contain unsaturation, and can be branched for example in a tert butyl or isopropyl group), aryl (phenyl, or substituted phenyl ring), and other functional groups. The reversible hydrophobic polypeptide complex can be dried or lyophilized to afford a dried reversible hydrophobic polypeptide complex.

Hydrophobation of a polypeptides through reversible hydrophobic modification may also be achieved by reacting amino groups on the polypeptide with hydrophobic amides derived from 2-propionic-3-methylmaleic anhydride to afford the reversible hydrophobic polypeptide complex (Naganawa et al. 1994; Hermanson 1996; Reddy et al. 2000; Dinand et al. 2002; Rozema et al. 2003). The present invention encompasses the reversible modification of polypeptides with compounds of general formula IV

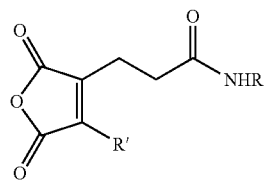

in which R is selected from the group consisting of alkyl, aryl, a steric group, or a targeting group, and R' is selected from the group of hydrogen, alkyl (from 1-30 carbons, can contain unsaturation, and can be branched for example in a tert butyl or isopropyl group), or aryl (phenyl, or substituted phenyl ring). The reversible hydrophobic polypeptide complex can be dried or lyophilized to afford a dried reversible hydrophobic polypeptide complex.

Figure 3:
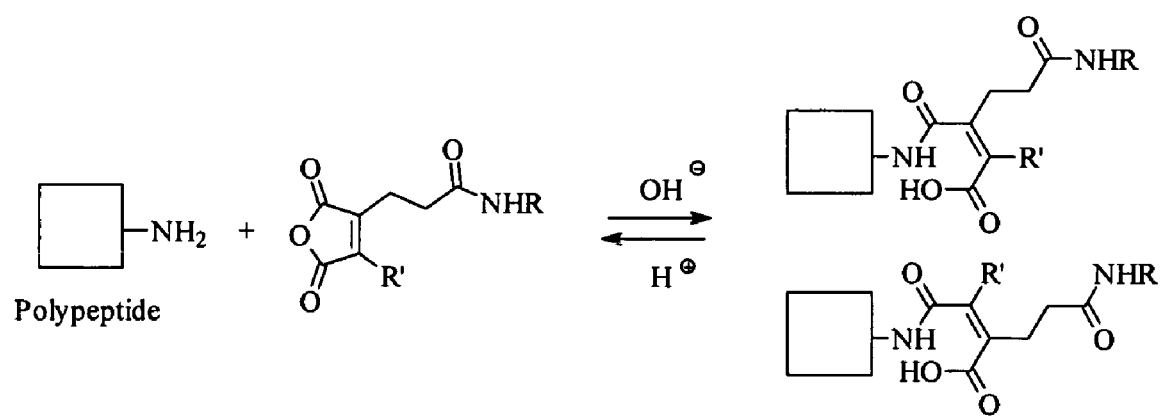
FIG. 3. Illustration of pH sensitive reversible hydrophobation of polypeptide using amphipathic maleic anhydride derivatives.

Maleic anhydrides react with amines on the polypeptide to form maleamic acids. This reaction is reversible. Maleamic acids are known to be stable under basic conditions, but hydrolyze under acidic conditions. In acidic conditions, the amide bond formed during the reaction between the amine and the anhydride is cleaved to yield the original unmodified amine and the maleic anhydride (FIG. 3)

Another embodiment of the present invention involves the association of the reversible hydrophobic polypeptide complex with one or more lipids, or with liposomes. By association in this case we mean that dried reversible hydrophobic polypeptide complex is mixed with the lipid or with liposomes. For example, the dried reversible hydrophobic polypeptide complex can be dissolved in an organic solution and added to an organic solution containing lipid(s). The resulting mixture can be dried to a film as is typically done in the art with liposomal preparations and hydrated with an aqueous solution to form the liposomes. Alternatively, the dried reversible hydrophobic polypeptide complex can be dissolved in an organic solution and added to an organic solution containing lipid(s). The resulting solution can be utilized directly for liposomal formation as is typically done in the art with liposomal preparations. Alternatively, the dried reversible hydrophobic polypeptide complex can be dissolved in an organic solution or in an organic/aqueous solution mixture and added to the lipid film to rehydrate the film, or can be added directly to liposomes. The lipid(s) and/or liposomes can posses additional functional groups. Additionally, the lipid(s) and liposomes can posses reactive groups to which functional groups can be attached.

Another embodiment of the present invention involves new methods for the application of lipid formulations onto cells in vitro. Traditionally, liposomal formulations have been widely utilized in the area of drug delivery and gene therapy. We were unable to observe cytoplasmic delivery of polypeptides into cells with a number of liposomes when using typical formulations: formation of liposomes in the presence of the polypeptide, dilution of the liposomes into culture media and incubation of the liposomes with cells for several hours. Incubation of cells with higher concentrations of liposomes/micelles for typical periods of time (one hour or longer) is frequently toxic to cells. In the present invention, more concentrated polypeptide formulations are added to cells in smaller volumes for shorter periods of time. Following a short incubation cell growth media is added. We show that mixing of liposomes with cells at high concentrations for short incubation times provides for delivery of polypeptides. This method departs from typical delivery systems where the polypeptide formulations are first diluted with media before incubation with cells at 37° C. for several hours.

Definitions

Chemical Bond—A chemical bond is a covalent or noncovalent bond.

Covalent Bond—A covalent bond is a chemical bond in which each atom of the bond contributes one electron to form a pair of electrons. A covalent bond can also mean a coordinate or dative bond.

Noncovalent Bond—A noncovalent bond or ionic bond is a bond in which electrons are transferred to atoms to afford charged atoms. Atoms of opposite charge can form an interaction.

Hydrophobation—Hydrophobation, or hydrophobic modification, is the act of associating a compound that possesses a hydrophobic group, such as a surfactant, with another compound via a chemical bond.

Noncovalent Hydrophobation—Noncovalent Hydrophobation or noncovalent hydrophobic modification is the formation of a noncovalent bond between a compound that possesses a hydrophobic group, such as a surfactant, and another compound.

Amphiphilic and Amphipathic Compounds—Amphipathic, or amphiphilic, compounds have both hydrophilic (water-soluble) and hydrophobic (water-insoluble) parts.

Lipid—Any of a diverse group of organic compounds that are insoluble in water, but soluble in organic solvents such as chloroform and benzene. Lipids contain both hydrophobic and hydrophilic sections. The term lipids are meant to include complex lipids, simple lipids, and synthetic lipids.

Complex Lipids—Complex lipids are the esters of fatty acids and include glycerides (fats and oils), glycolipids, phospholipids, and waxes.

Simple Lipids—Simple lipids include steroids and terpenes.

Synthetic Lipids—Synthetic lipids includes amides prepared from fatty acids wherein the carboxylic acid has been converted to the amide, synthetic variants of complex lipids in which one or more oxygen atoms has been substituted by another heteroatom (such as Nitrogen or Sulfur), and derivatives of simple lipids in which additional hydrophilic groups have been chemically attached. Synthetic lipids may contain one or more labile groups.

Fats—Fats are glycerol esters of long-chain carboxylic acids. Hydrolysis of fats yields glycerol and a carboxylic acid—a fatty acid. Fatty acids may be saturated or unsaturated (contain one or more double bonds).

Oils—Oils are esters of carboxylic acids or are glycerides of fatty acids.

Glycolipids—Glycolipids are sugar containing lipids. The sugars are typically galactose, glucose or inositol.

Wax—Waxes are any of various solid or semisolid substances generally being esters of fatty acids.

Fatty Acids—Fatty acids are considered the hydrolysis product of lipids (fats, waxes, and phosphoglycerides).

Surfactant—A surfactant is a surface active agent, such as a detergent or a lipid, which is added to a liquid to increase its spreading or wetting properties by reducing its surface tension. A surfactant refers to a compound that contains a polar group (hydrophilic) and a non-polar (hydrophobic) group on the same molecule. A cleavable surfactant is a surfactant in which the polar group may be separated from the nonpolar group by the breakage or cleavage of a chemical bond located between the two groups, or to a surfactant in which the polar or non-polar group or both may be chemically modified such that the detergent properties of the surfactant are destroyed.

Detergent—Detergents are compounds that are soluble in water and cause nonpolar substances to go into solution in water. Detergents have both hydrophobic and hydrophilic groups Micelle—Micelles are microscopic vesicles that contain amphipathic molecules but do not contain an aqueous volume that is entirely enclosed by a membrane. In micelles the hydrophilic part of the amphipathic compound is on the outside (on the surface of the vesicle). In inverse micelles the hydrophobic part of the amphipathic compound is on the outside. The inverse micelles thus contain a polar core that can solubilize both water and macromolecules within the inverse micelle.

Liposome—Liposomes are microscopic vesicles that contain amphipathic molecules and contain an aqueous volume that is entirely enclosed by a membrane.

Microemulsions—Microemulsions are isotropic, thermodynamically stable solutions in which substantial amounts of two immiscible liquids (water and oil) are brought into a single phase due to a surfactant or mixture of surfactants. The spontaneously formed colloidal particles are globular droplets of the minor solvent, surrounded by a monolayer of surfactant molecules. The spontaneous curvature, H0 of the surfactant monolayer at the oil/water interface dictates the phase behavior and microstructure of the vesicle. Hydrophilic surfactants produce oil in water (O/W) microemulsions (H0>0), whereas lipophilic surfactants produce water in oil (W/O) microemulsions.

Hydrophobic Groups—Hydrophobic groups indicate in qualitative terms that the chemical moiety is water-avoiding. Typically, such chemical groups are not water soluble, and tend not to form hydrogen bonds.

Hydrophilic Groups—Hydrophilic groups indicate in qualitative terms that the chemical moiety is water-preferring. Typically, such chemical groups are water soluble, and are hydrogen bond donors or acceptors with water.

Charge, Polarity, and Sign—The charge, polarity, or sign of a compound refers to whether or not a compound has lost one or more electrons (positive charge, polarity, or sign) or gained one or more electrons (negative charge, polarity, or sign).

Drying—Drying means removing the solvent from a sample, for example, removing the solvent from a complex under reduced pressure. Drying also means dehydrating a sample, or lyophilization of a sample.

Salt—A salt is any compound containing ionic bonds; i.e., bonds in which one or more electrons are transferred completely from one atom to another. Salts are ionic compounds that dissociate into cations and anions when dissolved in solution and thus increase the ionic strength of a solution.

Pharmaceutically Acceptable Salt—Pharmaceutically acceptable salt means both acid and base addition salts.

Pharmaceutically Acceptable Acid Addition Salt—A pharmaceutically acceptable acid addition salt is a salt that retains the biological effectiveness and properties of the free base, is not biologically or otherwise undesirable, and is formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid, and the like.

Pharmaceutically Acceptable Base Addition Salt—A pharmaceutically acceptable base addition salt is a salt that retains the biological effectiveness and properties of the free acid, is not biologically or otherwise undesirable, and is prepared from the addition of an inorganic organic base to the free acid. Salts derived from inorganic bases include, but are not limited to, sodium, potassium, calcium, lithium, ammonium, magnesium, zinc, and aluminum salts and the like. Salts derived from organic bases include, but are not limited to, salts of primary, secondary, and tertiary amines, such as methylamine, triethylamine, and the like.

Functional group—Functional groups include cell targeting signals, nuclear localization signals, compounds that enhance release of contents from endosomes or other intracellular vesicles (releasing signals), and other compounds that alter the behavior or interactions of the compound or complex to which they are attached. Additionally, a functional group also means a chemical functional group that can undergo further chemical reactions. Examples include but are not limited to hydroxyl groups, amine groups, thiols, carboxylic acids, aldehydes, and ketones.

Cell targeting signals—Cell targeting signals are any signals that enhance the association of the biologically active compound with a cell. These signals can modify a biologically active compound such as drug or nucleic acid and can direct it to a cell location (such as tissue) or location in a cell (such as the nucleus) either in culture or in a whole organism. The signal may increase binding of the compound to the cell surface and/or its association with an intracellular compartment. A cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. The ligand may seek a target within the cell membrane, on the cell membrane or near a cell. Binding of ligands to receptors typically initiates endocytosis. Chemical groups that react with thiol, sulfhydryl, or disulfide groups on cells can also be used to target many types of cells. Other targeting groups include molecules that interact with membranes such as lipids, fatty acids, cholesterol, dansyl compounds, and amphotericin derivatives. In addition viral proteins could be used to bind cells.

Nuclear localization signals—Nuclear localizing signals enhance the targeting of a pharmaceutical into proximity of the nucleus and/or its entry into the nucleus. Such nuclear transport signals can be a protein or a peptide such as the SV40 large T antigen NLS or the nucleoplasmin NLS. The nuclear transport proteins themselves could also function as NLS's. Several NLS peptides have been derived from the SV40 T antigen, hnRNP A1 protein, nucleoplasmin, c-myc, and M9 proteins.

Membrane active compounds—Membrane active polymers or compounds are molecules that are able to alter membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane.

Cell penetrating compounds—Cell penetrating compounds, which include cationic import peptides (also called peptide translocation domains, membrane translocation peptides, arginine-rich motifs, cell-penetrating peptides, and peptoid molecular transporters) are typically rich in arginine and lysine residues and are capable of crossing biological membranes. In addition, they are capable of transporting molecules to which they are attached across membranes. Examples include TAT peptide, VP22 peptide, and *Drosophila* antennapedia peptide. Cell penetrating compounds are not strictly peptides. Short, non-peptide polymers that are rich in amines or guanidinium groups are also capable of carrying molecules crossing biological membranes. Like membrane active peptides, cationic import peptides are defined by their activity rather than by strict amino acid sequence requirements.

Interaction Modifiers—An interaction modifier changes the way that a molecule interacts with itself or other molecules relative to molecule containing no interaction modifier. The result of this modification is that self-interactions or interactions with other molecules are either increased or decreased. For example cell targeting signals are interaction modifiers which change the interaction between a molecule and a cell or cellular component. Polyethylene glycol is an interaction modifier that decreases interactions between molecules and themselves and with other molecules.

Steric Stabilizer—A steric stabilizer is a long chain hydrophilic group that prevents aggregation by sterically hindering particle to particle or polymer to polymer electrostatic interactions. Examples include: alkyl groups, PEG chains, polysaccharides, alkyl amines. Electrostatic interactions are the noncovalent association of two or more substances due to attractive forces between positive and negative charges.

Chelator—A Chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X—(CR1-2)n)m units, where n=1-3 and m=3-8. The X and CR1-2 moieties can be substituted, or at a different oxidation states. X can be oxygen, nitrogen, or sulfur, carbon, phosphorous or any combination thereof. R can be H, C, O, S, N, P. The crown ether ring system is named as [(n+1)m crown m] for X=oxygen, as [(n+1)m azacrown m] when X=nitrogen, as [(n+1)m thiocrown m] when X=sulfur. In the case of two or more heteroatoms present in the ring the heteroatom positions are specified. For example, 12-crown-4,4-aminobenzo-12-crown-4,4-formylbenzo-12-crown-4,4-hydroxybenzo-12-crown-4,4-acryloylamidobenzo-12-crown-4,4-vinylbenzo-12-crown-4,15-crown-5,4-aminobenzo-15-crown-5,4-formylbenzo-15-crown-5,4-hydroxybenzo-15-crown-5,4-acryloylamidobenzo-15-crown-5,4-vinylbenzo-15-crown-5, 18-crown-6, benzo-18-crown-6,4-aminobenzo-18-crown-6, 4-formylbenzo-18-crown-6,4-hydroxybenzo-18-crown-6,4-acryloylamidobenzo-18-crown-6,4-vinylbenzo-18-crown-6, (18-crown-6)-2,3,11,12-tetracarboxylic acid, 2-hydroxymethyl-18-crown-6,2-aminomethyl-18-crown-6,1-aza-18-crown-6,16-crown-4,20-crown-4, and 18-crown-6, polyvinylbenzo 15-crown-5. A subset of crown ethers described as a cryptate contain a second $(—X—(C_{R1-}2)n)_z$ strand where z=3-8. The beginning X atom of the strand is an X atom in the $(—X—(C_{R1-}2)n)_m$ unit, and the terminal $5CH_2$ of the new strand is bonded to a second X atom in the $(—X—(C_{R1-}2)n)_m$ unit. Non-cyclic polydentate molecules containing $(—X—(C_{R1-}2)n)_m$ unit(s), where n=1-4 and m=1-8. The X and $C_{R1-2}$ moieties can be substituted, or at a different oxidation states. X can be oxygen, nitrogen, or sulfur, carbon, phosphorous or any combination thereof. For example di(ethylene glycol), hexa(ethylene glycol) and other polyglycols, tri(propylene glycol), ethylene diamine, N,N,N',N'-tetramethyldiethyldiamine, N,N,N',N'-ethylenediamine-tetraacetic acid, spermine, spermidine, diethylenetriamine, 1,3-diaminopropane, phenanthroline, 1,2-bis(dimethylphosphino)-ethane, 1,4-bis(dicyclohexylphosphino)butane, 1,2-bis(phenylphosphino)-ethane, 1,4-bis(phenylphosphino)-butane.

EXAMPLES

Example 1

Peptide Synthesis

To illustrate the utility of the invention in delivering peptides to cells, three different peptides were synthesized: a negatively charged peptide, a positively charged peptide and a charge neutral peptide. Peptide sequences were prepared using standard FastMoc FMOC Chemistry on an ABI 433A Peptide Synthesizer. Prior to deprotection and cleavage of the polypeptide from the resin, lissamine was added to fluorescently label the N-terminus of the polypeptide. The polypeptides were cleaved from the resin and deprotected using TFA/TIPS/H$_2$O (95/2.5/2.5) and purified by reverse phase HPLC. Molecular weights were verified using as PE SCIEX API150EX Mass Spectrometer.

```
NES sequence(NES; Seq ID 1)-         RLQLPPLERLTLD

Positive sequence(PosPep; Seq ID 2)- GKNRGKSAQAKRLR

Negative Sequence(NegPep; Seq ID 3)- GEGMEEGEFSEA
```

These sequences are merely indicated as examples, and are not intended to limit the scope of the invention in any way.

Example 2

Synthesis of Protein/Peptide Modification Reagents

1. Preparation of 2-(3-dodecyl-propionamide)-3-methyl maleic anhydride (CDM12): To a solution of 2-(3-propionic acid)-3-methyl maleic anhydride (11.1 mg, 0.060 mmol, Mirus Corporation) in dichloromethane (1.2 mL) was added oxalyl chloride (26 µL, 0.302 mmol, Aldrich Chemical Company) and diisopropylethylamine (10.5 µL, 0.060 mmol, Aldrich Chemical Company). The resulting solution was stirred at ambient temperature for 1 h and concentrated under reduced pressure. The resulting residue was resuspended in dichloromethane (1.2 mL) and dodecylamine (27.7 µL, 0.121 mmol, Aldrich Chemical Company) was added. The solution was stirred at ambient temperature for 12 h. The solution was concentrated under reduced pressure, and taken up in EtOAc (5 mL). The solution was extracted 3×10 mL 1N HCl, washed 1×10 mL H$_2$O, 1×10 mL brine, and concentrated to afford 19.5 mg (92%) of 2-(3-dodecyl-propionamide)-3-methyl maleic anhydride.

2. Preparation of 2-(3-butyl-propionamide)-3-methyl maleic anhydride (CDM4): To a solution of 2-(3-propionic acid)-3-methyl maleic anhydride (10.6 mg, 0.057 mmol, Mirus Corporation) in dichloromethane (1.2 mL) was added oxalyl chloride (25 µL, 0.288 mmol, Aldrich Chemical Company) and diisopropylethylamine (9.9 µL, 0.057 mmol, Aldrich Chemical Company). The resulting solution was stirred at ambient temperature for 1 h and concentrated under reduced pressure. The resulting residue was resuspended in dichloromethane (1.2 mL) and butylamine (11.3 µL, 0.114 mmol, Aldrich Chemical Company) was added. The solution was stirred at ambient temperature for 12 h. The solution was concentrated under reduced pressure, and taken up in EtOAc (5 mL). The solution was extracted 3×10 mL 1N HCl, washed 1×10 mL H$_2$O, 1×10 mL brine, and concentrated to afford 9.8 mg (72%) of 2-(3-butyl-propionamide)-3-methyl maleic anhydride.

Example 3

Polypeptide Modification

1. Preparation of NegPep-CPB: To a solution of NegPep (2.0 µg, 0.0011 µmol) in H$_2$O (25 µL) was added cetylpyridinium bromide (2.0 µg, 0.005 µmol, Aldrich Chemical Company). The resulting solution was vortexes, frozen, and lyophilized.

2. Preparation of NegPep-CTAB: To a solution of NegPep (2.0 µg, 0.0011 µmol) in H$_2$O (25 µL) was added cetyltrimethyl-ammonium bromide (1.0 µg, 0.0027 µmol, Aldrich Chemical Company). The resulting solution was vortexes, frozen, and lyophilized.

3. Preparation of NegPep-DPC: To a solution of NegPep (2.0 µg, 0.0011 µmol) in H$_2$O (25 µL) was added dodecylpyridinium chloride (1.6 µg, 0.0056 µmol, Aldrich Chemical Company) and the solution was vortexes. The solution was frozen and lyophilized.

4. Preparation of NegPep-DAB: To a solution of NegPep (2.0 µg, 0.0011 µmol) in H$_2$O (25 µL) was added dodecyltrimethylammonium bromide (1.7 µg, 0.0055 µmol, Aldrich Chemical Company) and the solution was vortexes. The solution was frozen and lyophilized.

5. Preparation of NegPep-CDAB: To a solution of NegPep (2.0 µg, 0.0011 µmol) in H$_2$O (25 µL) was added cetyldimethylethylammonium bromide (2.1 µg, 0.0055 µmol, Aldrich Chemical Company) and the resulting solution was vortexes. The solution was frozen and lyophilized.

6. Preparation of PosPep-TOPPS: To a solution of PosPep (2.0 μg, 0.00095 μmol) in H$_2$O (25 μL) was added TOPPS (1.0 μg, 0.0029 μmol, Aldrich Chemical Company) and the resulting solution was vortexes. The solution was frozen and lyophilized.

7. Preparation of PosPep-CDM12-0.45: To a solution of PosPep (2.0 μg, 0.00095 μmol) in H$_2$O (25 μL) was added CDM12 (0.15 μg, 0.00043 μmol) and the resulting solution was vortexes. The mixture was frozen and lyophilized.

8. Preparation of NES-CDM12-1: To a solution of NES peptide (10 μg, 0.0048 μmol) in H$_2$O:EtOH (20 μL, 1:1) was added CDM12 (1.7 μg, 0.0048 μmol, 1 mg/mL solution in EtOH) and diisopropylaminomethyl-polystyrene (3 mg, Fluka Chemical Company). The resulting mixture was mixed for 30 min and centrifuged to remove the solid support base.

9. Preparation of NES-CDM12-2: To a solution of NES peptide (10 μg, 0.0048 μmol) in H$_2$O:EtOH (20 μL, 1:1) was added CDM12 (3.4 μg, 0.0096 μmol, 1 mg/mL solution in EtOH) and diisopropylaminomethyl-polystyrene (3 mg, Fluka Chemical Company). The resulting mixture was mixed for 30 min and centrifuged to remove the solid support base.

10. Preparation of PosPep-CDM12-1: To a solution of PosPep (10 μg, 0.0047 μmol) in H$_2$O:EtOH (20 μL, 1:1) was added CDM12 (1.7 μg, 0.0047 μmol, 1 mg/mL solution in EtOH) and diisopropylaminomethyl-polystyrene (3 mg, Fluka Chemical Company). The resulting mixture was mixed for 30 min and centrifuged to remove the solid support base.

11. Preparation of PosPep-CDM12-2: To a solution of PosPep (10 μg, 0.0047 μmol) in H$_2$O:EtOH (20 μL, 1:1) was added CDM12 (3.3 μg, 0.0094 μmol, 1 mg/mL solution in EtOH) and diisopropylaminomethyl-polystyrene (3 mg, Fluka Chemical Company). The resulting mixture was mixed for 30 min and centrifuged to remove the solid support base.

12. Preparation of NegPep-CDM12-1: To a solution of NegPep (10 μg, 0.0055 μmol) in H$_2$O:EtOH (20 μL, 1:1) was added CDM12 (2.2 μg, 0.0055 μmol, 1 mg/mL solution in EtOH) and diisopropylaminomethyl-polystyrene (3 mg, Fluka Chemical Company). The resulting mixture was mixed for 30 min and centrifuged to remove the solid support base.

13. Preparation of NegPep-CDM12-2: To a solution of NegPep (10 μg, 0.0055 μmol) in H$_2$O:EtOH (20 μL, 1:1) was added CDM12 (4.3 μg, 0.011 μmol, 1 mg/mL solution in EtOH) and diisopropylaminomethyl-polystyrene (3 mg, Fluka Chemical Company). The resulting mixture was mixed for 30 min and centrifuged to remove the solid support base.

14. Preparation of NES-MK10-1: To a solution of NES peptide (10 μg, 0.0048 μmol) in H$_2$O:EtOH (20 μL, 1:1) was added 2-dceyl-1,4,7,10,13,16 hexaoxacyclooctadecane (1.9 μg, 0.0048 μmol, Merck, 1 mg/mL solution in EtOH). The resulting solution was mixed for 30 min prior to use.

15. Preparation of NES-MK10-2: To a solution of NES peptide (10 μg, 0.0048 μmol) in H$_2$O:EtOH (20 μL, 1:1) was added 2-dceyl-1,4,7,10,13,16 hexaoxacyclooctadecane (3.88 μg, 0.0096 μmol, Merck, 1 mg/mL solution in EtOH). The resulting solution was mixed for 30 min prior to use.

16. Preparation of PosPep-MK10-1: To a solution of PosPep peptide (10 μg, 0.0047 μmol) in H$_2$O:EtOH (20 μL, 1:1) was added 2-dceyl-1,4,7,10,13,16 hexaoxacyclooctadecane (1.9 μg, 0.0047 μmol, Merck, 1 mg/mL solution in EtOH). The resulting solution was mixed for 30 min prior to use.

17. Preparation of PosPep-MK10-2: To a solution of PosPep peptide (10 μg, 0.0047 μmol) in H$_2$O:EtOH (20 μL, 1:1) was added 2-dceyl-1,4,7,10,13,16 hexaoxacyclooctadecane (3.83 μg, 0.0095 μmol, Merck, 1 mg/mL solution in EtOH). The resulting solution was mixed for 30 min prior to use.

18. Preparation of NegPep-MK10-1: To a solution of NegPep peptide (10 μg, 0.0055 μmol) in H$_2$O:EtOH (20 μL, 1:1) was added 2-dceyl-1,4,7,10,13,16 hexaoxacyclooctadecane (2.2 μg, 0.0055 μmol, Merck, 1 mg/mL solution in EtOH). The resulting solution was mixed for 30 min prior to use.

19. Preparation of NegPep-MK10-2: To a solution of NegPep peptide (10 μg, 0.0055 μmol) in H$_2$O:EtOH (20 μL, 1:1) was added 2-dceyl-1,4,7,10,13,16 hexaoxacyclooctadecane (4.5 μg, 0.011 μmol, Merck, 1 mg/mL solution in EtOH). The resulting solution was mixed for 30 min prior to use.

20. Preparation of NES-Tos-MK10-1: To a solution of NES peptide (10 μg, 0.0048 μmol) in H$_2$O:EtOH (20 μL, 1:1) was added sodium p-toluenesulfonate (0.93 μg, 0.0048 μmol, Aldrich Chemical Company) as a 1 mg/mL solution in H$_2$O, followed by 2-dceyl-1,4,7,10,13,16 hexaoxacyclooctadecane (1.9 μg, 0.0048 μmol, Merck, 1 mg/mL solution in EtOH). The resulting solution was mixed for 30 min prior to use.

21. Preparation of NES-Tos-MK10-2: To a solution of NES peptide (10 μg, 0.0048 μmol) in H$_2$O:EtOH (20 μL, 1:1) was added sodium p-toluenesulfonate (1.9 μg, 0.0096 μmol, Aldrich Chemical Company) as a 1 mg/mL solution in H$_2$O, followed by 2-dceyl-1,4,7,10,13,16 hexaoxacyclooctadecane (3.88 μg, 0.0096 μmol, Merck, 1 mg/mL solution in EtOH). The resulting solution was mixed for 30 min prior to use.

22. Preparation of PosPep-Tos-MK10-1: To a solution of PosPep peptide (10 μg, 0.0047 μmol) in H$_2$O:EtOH (20 μL, 1:1) was added sodium p-toluenesulfonate (0.91 μg, 0.0047 μmol, Aldrich Chemical Company) as a 1 mg/mL solution in H$_2$O, followed by 2-dceyl-1,4,7,10,13,16 hexaoxacyclooctadecane (1.9 μg, 0.0047 μmol, Merck, 1 mg/mL solution in EtOH). The resulting solution was mixed for 30 min prior to use.

23. Preparation of PosPep-Tos-MK10-2: To a solution of PosPep peptide (10 μg, 0.0047 μmol) in H$_2$O:EtOH (20 μL, 1:1) was added sodium p-toluenesulfonate (1.8 μg, 0.0095 μmol, Aldrich Chemical Company) as a 1 mg/mL solution in H$_2$O, followed by 2-dceyl-1,4,7,10,13,16 hexaoxacyclooctadecane (3.83 μg, 0.0095 μmol, Merck, 1 mg/mL solution in EtOH). The resulting solution was mixed for 30 min prior to use.

24. Preparation of NegPep-Tos-MK10-1: To a solution of NegPep peptide (10 μg, 0.0055 μmol) in H$_2$O:EtOH (20 μL, 1:1) was added sodium p-toluenesulfonate (1.1 μg, 0.0055 μmol, Aldrich Chemical Company) as a 1 mg/mL solution in H$_2$O, followed by 2-dceyl-1,4,7,10,13,16 hexaoxacyclooctadecane (2.2 μg, 0.0055 μmol, Merck, 1 mg/mL solution in EtOH). The resulting solution was mixed for 30 min prior to use.

25. Preparation of NegPep-Tos-MK10-2: To a solution of NegPep peptide (10 μg, 0.0055 μmol) in H$_2$O:EtOH (20 μL, 1:1) was added sodium p-toluenesulfonate (2.1 μg, 0.0055 μmol, Aldrich Chemical Company) as a 1 mg/mL solution in H$_2$O, followed by 2-dceyl-1,4,7,10,13,16 hexaoxacyclooctadecane (4.5 μg, 0.011 μmol, Merck, 1 mg/mL solution in EtOH). The resulting solution was mixed for 30 min prior to use.

26. Preparation of albumin-dimethyloctadecylsilane: Rhodamine-labeled Bovine Serum Albumin (BSA, Sigma Chemical Company) was dissolved in $H_2O$ to a final concentration of 20 mg/mL. A 1 μL (20 μg) aliquot of the stock solution was taken and diluted with $H_2O$ to a final concentration of 1 mg/mL. To 2 μL of this solution was added 100 μL of chloroform, followed by chlorodimethyloctadecylsilane (250 μg in 5 μL chloroform, Aldrich Chemical Company). The resulting solution was sonicated for 10 sec and dried under vacuum. The resulting film was hydrated with 50 μL PBS.

Example 4

Formulations for Protein/Peptide Delivery

1. Preparation of DOTAP-Cl/NegPep-CPB: To a solution of NegPep (2.0 μg, 0.0011 μmol) in $H_2O$ (25 μL) was added cetylpyridinium bromide (2.0 μg, 0.005 μmol, Aldrich Chemical Company). The resulting solution was vortexes, frozen, and lyophilized. The freeze dried material was brought up in $CHCl_3$ (50 μL). DOTAP chloride (8.5 μL of 1 μg/μL solution in $CHCl_3$, 0.012 μmol, Avanti Polar Lipids, Inc) was added and the solution was vortexes. The solution was dried into a film under $N_2$ and placed under vacuum overnight.
2. Preparation of DOTAP-Cl/NegPep-CTAB: To a solution of NegPep (2.0 μg, 0.0011 μmol) in $H_2O$ (25 μL) was added cetyltrimethyl-ammonium bromide (1.0 μg, 0.0027 μmol, Aldrich Chemical Company). The resulting solution was vortexes, frozen, and lyophilized. The freeze dried material was brought up in $CHCl_3$ (50 μL). DOTAP (8.5 μg, 0.012 μmol, Avanti Polar Lipids, Inc) was added and the solution was vortexes. The solution was dried into a film under $N_2$ and placed under vacuum overnight
3. Preparation of DOTAP-Cl/NegPep-DPC: To a solution of NegPep (2.0 μg, 0.0011 μmol) in $H_2O$ (25 μL) was added dodecylpyridinium chloride (1.6 μg, 0.0056 μmol, Aldrich Chemical Company) and the solution was vortexes. The solution was frozen and lyophilized. The freeze dried material was brought up in $CHCl_3$ (50 μL). DOTAP (8.5 μg, 0.012 μmol, Avanti Polar Lipids, Inc) was added and the solution was vortexes. The mixture was dried into a film under $N_2$ and placed under vacuum overnight
4. Preparation of DOTAP-Cl/NegPep-DAB: To a solution of NegPep (2.0 μg, 0.0011 μmol) in $H_2O$ (25 μL) was added dodecyltrimethylammonium bromide (1.7 μg, 0.0055 μmol, Aldrich Chemical Company) and the solution was vortexes. The solution was frozen and lyophilized. The freeze dried material was brought up in $CHCl_3$ (50 μL). DOTAP (8.5 μg, 0.012 μmol, Avanti Polar Lipids, Inc) was added and the resulting solution was vortexes. The mixture was dried into a film under $N_2$ and placed under vacuum overnight
5. Preparation of DOTAP-Cl/NegPep-CDAB: To a solution of NegPep (2.0 μg, 0.0011 μmol) in $H_2O$ (25 μL) was added cetyldimethylethylammonium bromide (2.1 μg, 0.0055 μmol, Aldrich Chemical Company) and the resulting solution was vortexes. The solution was frozen and lyophilized. The freeze dried material was brought up in $CHCl_3$ (50 μL). DOTAP (8.5 μg, 0.012 μmol, Avanti Polar Lipids, Inc) was added and the resulting solution was vortexes. The mixture was dried into a film under $N_2$ and placed under vacuum overnight
6. Preparation of DOTAP-Cl/PosPep-TOPPS: To a solution of PosPep (2.0 μg, 0.00095 μmol) in $H_2O$ (25 μL) was added TOPPS (1.0 μg, 0.0029 μmol, Aldrich Chemical Company) and the resulting solution was vortexes. The solution was frozen and lyophilized. The freeze dried material was brought up in $CHCl_3$ (50 μL). DOTAP (8.5 μg, 0.012 μmol, Avanti Chemical Company) was added and the solution was vortexes. The mixture was dried into a film under $N_2$ and placed under vacuum overnight.
7. Preparation of DOTAP-Cl/PosPep-CDM12-0.45: To a solution of PosPep (2.0 μg, 0.00095 μmol) in $H_2O$ (25 μL) was added CDM12 (0.15 μg, 0.00043 μmol) and the resulting solution was vortexes. The mixture was frozen and lyophilized. The freeze dried material was brought up in $CHCl_3$ (50 μL). DOTAP (8.5 μg, 0.012 μmol, Avanti Chemical Company) was added and the solution was vortexes. The mixture was dried into a film under $N_2$ and placed under vacuum overnight.
8. Preparation of DOTAP-Cl/NES: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES (2 μg) in $H_2O$:EtOH (4 μL, 1:1) and PBS (30 μL). The resulting mixture was vortexes, and allowed to hydrate for 15 min, followed by vortexing and sonication (<5 sec).
9. Preparation of DOTAP-Cl/NES-CDM12-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-CDM12-1 (2 μg) in $H_2O$:EtOH (4 μL, 1:1) and PBS (30 μL). The resulting mixture was vortexes, and allowed to hydrate for 15 min, followed by vortexing and sonication (<5 sec).
10. Preparation of DOTAP-Cl/NES-CDM12-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-CDM12-2 (2 μg) in $H_2O$:EtOH (4 μL, 1:1) and PBS (30 μL). The resulting mixture was vortexes, and allowed to hydrate for 15 min, followed by vortexing and sonication (<5 sec).
11. Preparation of DOTAP-Cl/PosPep: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep (2 μg) in $H_2O$ (2 μL) and PBS (30 μL). The resulting mixture was vortexes, and allowed to hydrate for 15 min, followed by vortexing and sonication (<5 sec).
12. Preparation of DOTAP-Cl/PosPep-CDM12-1: DOTAP-Cl (10 μg, 1 g/μL in chloroform, Avanti Polar Lipids, Inc) was added to a micro centrifuge tube, concentrated into a film under a stream of nitrogen, and then placed under vacuum. To the lipid film was added a solution of PosPep-CDM12-1 (2 μg) in $H_2O$:EtOH (4 μL, 1:1) and PBS (30 μL). The resulting mixture was vortexes, and allowed to hydrate for 15 min, followed by vortexing and sonication (<5 sec).
13. Preparation of DOTAP-Cl/PosPep-CDM12-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-CDM12-2 (2 μg) in $H_2O$:EtOH (4 μL, 1:1) and PBS (30

μL). The resulting mixture was vortexes, and allowed to hydrate for 15 min, followed by vortexing and sonication (<5 sec).

14. Preparation of DOTAP-Cl/NegPep: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NegPep (2 μg) in $H_2O$ (2 μL) and PBS (30 μL). The resulting mixture was vortexes, and allowed to hydrate for 15 min, followed by vortexing and sonication (<5 sec).

15. Preparation of DOTAP-Cl/NegPep-CDM12-1: DOTAP-Cl (10 μg, 1g/μL in chloroform, Avanti Polar Lipids, Inc) was added to a micro centrifuge tube, concentrated into a film under a stream of nitrogen, and then placed under vacuum. To the lipid film was added a solution of NegPep-CDM12-1 (2 μg) in $H_2O$:EtOH (4 μL, 1:1) and PBS (30 μL). The resulting mixture was vortexes, and allowed to hydrate for 15 min, followed by vortexing and sonication (<5 sec).

16. Preparation of DOTAP-Cl/NegPep-CDM12-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NegPep-CDM12-2 (2 μg) in $H_2O$:EtOH (4 μL, 1:1) and PBS (30 μL). The resulting mixture was vortexes, and allowed to hydrate for 15 min, followed by vortexing and sonication (<5 sec).

17. Preparation of DOTAP-Cl/NES-MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-MK10-1 (2 μg) in $H_2O$:EtOH (4 μL, 1:1) and PBS (30 μL). The resulting mixture was vortexes, and allowed to hydrate for 15 min, followed by vortexing and sonication (<5 sec).

18. Preparation of DOTAP-Cl/NES-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

19. Preparation of DOTAP-Cl/PosPep-MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-MK10-1 (2 μg) in $H_2O$:EtOH (4 μL, 1:1) and PBS (30 μL). The resulting mixture was vortexes, and allowed to hydrate for 15 min, followed by vortexing and sonication (<5 sec).

20. Preparation of DOTAP-Cl /PosPep-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-CDM12-2 (2 μg) in $H_2O$:EtOH (4 μL, 1:1) and PBS (30 μL). The resulting mixture was vortexes, and allowed to hydrate for 15 min, followed by vortexing and sonication (<5 sec).

21. Preparation of DOTAP-Cl/NegPep-MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

22. Preparation of DOTAP-Cl/ NegPep-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NegPep-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

23. Preparation of DOTAP-Cl/NES-Tos-MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-Tos-MK10-1 (2 μg) in $H_2O$:EtOH (4 μL, 1:1) and PBS (30 μL). The resulting mixture was vortexes, and allowed to hydrate for 15 min, followed by vortexing and sonication (<5 sec).

24. Preparation of DOTAP-Cl/NES-Tos-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-Tos-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

25. Preparation of DOTAP-Cl/PosPep-Tos -MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-Tos-MK10-1 (2 μg) in $H_2O$:EtOH (4 μL, 1:1) and PBS (30 μL). The resulting mixture was vortexes, and allowed to hydrate for 15 min, followed by vortexing and sonication (<5 sec).

26. Preparation of DOTAP-Cl/PosPep-Tos-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-Tos-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

27. Preparation of DOTAP-Cl/NegPep-Tos-MK10-1: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NegPep-Tos-MK10-1 (2 μg) in $H_2O$:EtOH (4 μL, 1:1) and PBS (30 μL). The resulting mixture was vortexes, and allowed to hydrate for 15 min, followed by vortexing and sonication (<5 sec).

28. Preparation of DOTAP-Cl/NegPep-Tos-MK10-2: DOTAP-Cl (10 μg, 1 μg/μL in chloroform, Avanti Polar Lipids, Inc) was added to a micro centrifuge tube, concentrated into a film under a stream of nitrogen, and then placed under vacuum. To the lipid film was added a solution of NegPep-Tos-MK10-2 (2 μg) in $H_2O$:EtOH (4 μL, 1:1) and PBS (30 μL). The resulting mixture was vortexes, and allowed to hydrate for 15 min, followed by vortexing and sonication (<5 sec).

29. Preparation of DOTAP-Cl/Cholesterol/NES: DOTAP-Cl (10 μg, 1 μg/μL in chloroform, Avanti Polar Lipids, Inc)

and Cholesterol (5 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES (2 μg) in $H_2O$:EtOH (4 μL, 1:1) and PBS (30 μL). The resulting mixture was vortexes, and allowed to hydrate for 15 min, followed by vortexing and sonication (<5 sec).

30. Preparation of DOTAP-Cl/Cholesterol/NES-CDM12-1: DOTAP-Cl (10 μg, 1 μg/μL in chloroform, Avanti Polar Lipids, Inc) and Cholesterol (5 μg, 1 μg/μL in chloroform, Avanti Polar Lipids, Inc) was added to a micro centrifuge tube, concentrated into a film under a stream of nitrogen, and then placed under vacuum. To the lipid film was added a solution of NES-CDM12-1 (2 μg) in $H_2O$:EtOH (4 μL, 1:1) and PBS (30 μL). The resulting mixture was vortexes, and allowed to hydrate for 15 min, followed by vortexing and sonication (<5 sec).

31. Preparation of DOTAP-Cl/Cholesterol/PosPep: DOTAP-Cl (10 μg, 1 μg/μL in chloroform, Avanti Polar Lipids, Inc) and Cholesterol (5 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep (2 μg) in $H_2O$ (2 μL) and PBS (30 μL). The resulting mixture was vortexes, and allowed to hydrate for 15 min, followed by vortexing and sonication (<5 sec).

32. Preparation of DOTAP-Cl/Cholesterol/PosPep-CDM12-1: DOTAP-Cl (10 μg, 1 μg/μL in chloroform, Avanti Polar Lipids, Inc) and Cholesterol (5 μg, 1 μg/μL in chloroform, Avanti Polar Lipids, Inc) was added to a micro centrifuge tube, concentrated into a film under a stream of nitrogen, and then placed under vacuum. To the lipid film was added a solution of PosPep-CDM12-1 (2 μg) in $H_2O$:EtOH (4 μL, 1:1) and PBS (30 μL). The resulting mixture was vortexes, and allowed to hydrate for 15 min, followed by vortexing and sonication (<5 sec).

33. Preparation of DOTAP-Cl/NegPep-CPB: To a solution of NegPep (2.0 μg, 0.0011 μmol) in $H_2O$ (25 μL) was added cetylpyridinium bromide (0.44 μg, 0.0011 μmol, Aldrich Chemical Company). The resulting solution was vortexes, frozen and lyophilized. The freeze dried material was brought up in $CHCl_3$ (50 μL). DOTAP-Cl (10 μg of 1 μg/μL in $CHCl_3$, 0.014 μmol, Avanti Polar Lipids, Inc) was added and vortexes. The mixture was dried into a film under $N_2$ and placed under vacuum overnight.

34. Preparation of DDAB/NegPep-CPB: To a solution of NegPep (2.0 μg, 0.0011 μmol) in $H_2O$ (25 μL) was added cetylpyridinium bromide (0.44 μg, 0.0011 μmol, Aldrich Chemical Company). The resulting solution was vortexes, frozen and lyophilized. The freeze dried material was brought up in $CHCl_3$ (50 μL). Dodecyldimethylammonium bromide (6.0 μg of 1 μg/μL in EtOH, 0.015 μmol, Aldrich Chemical Company) was added and vortexes. The mixture was dried into a film under $N_2$ and placed under vacuum overnight.

35. Preparation of $Me_3$Sphing/NegPep-CPB: To a solution of NegPep (2.0 μg, 0.0011 μmol) in $H_2O$ (25 μL) was added cetylpyridinium bromide (0.44 μg, 0.0011 μmol, Aldrich Chemical Company). The resulting solution was vortexes, frozen and lyophilized. The freeze dried material was brought up in $CHCl_3$ (50 μL). N,N,N-Trimethylsphingosine (5.0 μg of 1 μg/μL in $CHCl_3$, 0.015 μmol, Avanti Polar Lipids, Inc) was added and vortexes. The mixture was dried into a film under $N_2$ and placed under vacuum overnight.

36. Preparation of DOTAP-Cl/NegPep-DPC: To a solution of NegPep (2.0 μg, 0.0011 μmol) in $H_2O$ (25 μL) was added dodecylpyridinium chloride (0.31 μg, 0.0011 μmol, Aldrich Chemical Company). The resulting solution was vortexes, frozen and lyophilized. The freeze dried material was brought up in $CHCl_3$ (50 μL). DOTAP-Cl (10 μg of 1 μg/μL in $CHCl_3$, 0.014 μmol, Avanti Polar Lipids, Inc) was added and vortexes. The mixture was dried into a film under $N_2$ and placed under vacuum overnight.

37. Preparation of DDAB/NegPep-DPC: To a solution of NegPep (2.0 μg, 0.0011 μmol) in $H_2O$ (25 μL) was added dodecylpyridinium chloride (0.31 μg, 0.0011 μmol, Aldrich Chemical Company). The resulting solution was vortexes, frozen and lyophilized. The freeze dried material was brought up in $CHCl_3$ (50 μL). Dodecyldimethylammonium bromide (6.0 μg of 1 μg/μL in EtOH, 0.015 μmol, Aldrich Chemical Company) was added and vortexes. The mixture was dried into a film under $N_2$ and placed under vacuum overnight.

38. Preparation of $Me_3$Sphing/NegPep-DPC: To a solution of NegPep (2.0 μg, 0.0011 μmol) in $H_2O$ (25 μL) was added dodecylpyridinium chloride (0.31 μg, 0.0011 μmol, Aldrich Chemical Company). The resulting solution was vortexes, frozen and lyophilized. The freeze dried material was brought up in $CHCl_3$ (50 μL). N,N,N-Trimethylsphingosine (5.0 μg of 1 μg/μL in $CHCl_3$, 0.015 μmol, Avanti Polar Lipids, Inc) was added and vortexes. The mixture was dried into a film under $N_2$ and placed under vacuum overnight.

39. Preparation of DOTAP-Cl/NegPep-DDAB: To a solution of NegPep (2.0 μg, 0.0011 μmol) in $H_2O$ (25 μL) was added dodecyldimethylammonium bromide (0.45 μg, 0.0011 μmol, Aldrich Chemical Company). The resulting solution was vortexes, frozen and lyophilized. The freeze dried material was brought up in $CHCl_3$ (50 μL). DOTAP-Cl (10 μg of 1 μg/μL in $CHCl_3$, 0.014 μmol, Avanti Polar Lipids, Inc) was added and vortexes. The mixture was dried into a film under $N_2$ and placed under vacuum overnight.

40. Preparation of DOTAP-Cl/NegPep-MC753: To a solution of NegPep (2.0 μg, 0.0011 μmol) in $H_2O$ (25 μL) was added MC753 (0.45 μg, 0.0011 μmol, Mirus Corporation). The resulting solution was vortexes, frozen and lyophilized. The freeze dried material was brought up in $CHCl_3$ (50 μL). DOTAP-Cl (10 μg of 1 μg/μL in $CHCl_3$, 0.014 μmol, Avanti Polar Lipids, Inc) was added and vortexes. The mixture was dried into a film under $N_2$ and placed under vacuum overnight.

41. Preparation of DDAB/NegPep-MC753: To a solution of NegPep (2.0 μg, 0.0011 μmol) in $H_2O$ (25 μL) was added MC753 (1.4 μg, 0.0034 μmol, Mirus Corporation). The resulting solution was vortexes, frozen and lyophilized. The freeze dried material was brought up in $CHCl_3$ (50 μL). Dodecyldimethylammonium bromide (6.0 μg of 1 μg/μL in EtOH, 0.015 μmol, Aldrich Chemical Company) was added and vortexes. The mixture was dried into a film under $N_2$ and placed under vacuum overnight.

42. Preparation of DOTAP-Cl/NegPep: A solution of NegPep (2.0 μg, 0.0011 μmol) in $H_2O$ (25 μL) was vortexes, frozen and lyophilized. The freeze dried material was brought up in $CHCl_3$ (50 μL). DOTAP-Cl (10 μg of 1 μg/μL in $CHCl_3$, 0.014 μmol, Avanti Polar Lipids, Inc) was added and vortexes. The mixture was dried into a film under $N_2$ and placed under vacuum overnight.

43. Preparation of DDAB/NegPep: A solution of NegPep (2.0 μg, 0.0011 μmol) in $H_2O$ (25 μL) was vortexes, frozen and lyophilized. The freeze dried material was brought up in $CHCl_3$ (50 μL). Dodecyldimethylammonium bromide (6.0

µg of 1 µg/µL in EtOH, 0.015 µmol, Aldrich Chemical Company) was added and vortexes. The mixture was dried into a film under $N_2$ and placed under vacuum overnight.

44. Preparation of Me3Sphing/NegPep: A solution of NegPep (2.0 µg, 0.0011 µmol) in $H_2O$ (25 µL) was vortexes, frozen and lyophilized. The freeze dried material was brought up in $CHCl_3$ (50 µL). N,N,N-Trimethylsphingosine (5.0 µg of 1 µg/µL in $CHCl_3$, 0.015 µmol, Avanti Polar Lipids, Inc) was added and vortexes. The mixture was dried into a film under $N_2$ and placed under vacuum overnight.

45. Preparation of DOTAP-Cl/PosPep-CDM12 (1:1): To a solution of PosPep (2.0 µg, 0.00095 µmol) in $H_2O$ (25 µL) was added CDM12 (0.33 µg, 0.00095 µmol, Mirus Corporation). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

46. Preparation of DOTAP-Cl/PosPep-CDM12 (1:6): To a solution of PosPep (2.0 µg, 0.00095 µmol) in $H_2O$ (25 µL) was added CDM12 (2.0 µg, 0.0057 µmol, Mirus Corporation). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

47. Preparation of DOTAP-Cl/PosPep-AOT: To a solution of PosPep (2.0 µg, 0.00095 µmol) in $H_2O$ (25 µL) was added dioctylsulfosuccinate sodium salt (0.42 µg, 0.00095 µmol, Aldrich Chemical Company). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

48. Preparation of AOT/PosPep: A solution of PosPep (2.0 µg, 0.00095 µmol) in $H_2O$ (25 µL) was vortexes, frozen and lyophilized. The freeze dried material was brought up in $CHCl_3$ (50 µL). Dioctylsulfosuccinate sodium salt (6.0 µg of 1 µg/µL in EtOH, 0.011 µmol, Aldrich Chemical Company) was added and vortexes. The mixture was dried into a film under $N_2$ and placed under vacuum overnight.

49. Preparation of DOTAP-Cl/PosPep: A solution of PosPep (2.0 µg, 0.00095 µmol) in $H_2O$ (25 µL) was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

50. Preparation of DOTAP-Cl/NES-Zwitt 3-12 (1-3): To a solution of NES (2.0 µg, 0.00095 µmol) in $H_2O$ (25 µL) was added Zwittergent 3-12 (1.0 µg, 0.0030 µmol, Calbiochem). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

51. Preparation of DOTAP-Cl/NES-Zwitt 3-12 (1:6): To a solution of NES (2.0 µg, 0.00095 µmol) in $H_2O$ (25 µL) was added Zwittergent 3-12 (2.0 µg, 0.0060 µmol, Calbiochem). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

52. Preparation of DOTAP-Cl/NES-Zwitt 3-14 (1:3): To a solution of NES (2.0 µg, 0.00095 µmol) in $H_2O$ (25 µL) was added Zwittergent 3-14 (1.0 µg, 0.0027 µmol, Calbiochem). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

53. Preparation of DOTAP-Cl/NES-Zwitt 3-14 (1:6): To a solution of NES (2.0 µg, 0.00095 µmol) in $H_2O$ (25 µL) was added Zwittergent 3-14 (2.0 µg, 0.0055 µmol, Calbiochem). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

54. Preparation of DOTAP-Cl/NES-CDM12 (1:2): To a solution of NES (2.0 µg, 0.00095 µmol) in $H_2O$ (25 µL) was added CDM12 (0.67 µg, 0.0019 µmol, Calbiochem). The resulting solution was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

55. Preparation of DOTAP-Cl/NES: A solution of NES (2.0 µg, 0.00095 µmol) in $H_2O$ (25 µL) was vortexes, frozen and lyophilized. The freeze dried material was brought up in $CHCl_3$ (50 µL). DOTAP-Cl (10 µg of 1 µg/µL in $CHCl_3$, 0.014 µmol, Avanti Polar Lipids, Inc) was added and vortexes. The mixture was dried into a film under $N_2$ and placed under vacuum overnight.

56. Preparation of DOTAP-Cl/Cholesterol/NES: DOTAP-Cl (10 µg, 0.2 µg/µL in chloroform, Avanti Polar Lipids, Inc) and Cholesterol (5 µg, 0.1 µg/µL in chloroform, Avanti Polar Lipids, Inc) was added to a micro centrifuge tube and air dried to produce a lipid film. To the lipid film was added a solution of NES (2 µg) in PBS (30 µL). The resulting mixture was vortexes, and allowed to hydrate for 10-30 min, followed by brief gentle vortexing and bath sonication (5 sec).

57. Preparation of DOTAP-Cl/Cholesterol/Oleic acid/PosPep: DOTAP-Cl (10 µg, 0.2 µg/µL in chloroform, Avanti Polar Lipids, Inc) and Cholesterol (2.5 µg, 0.05 µg/µL in chloroform, Avanti Polar Lipids, Inc) and Oleic Acid (0.2 µg, 0.004 µg/µl in chloroform, Sigma) was added to a micro centrifuge tube and air dried to produce a lipid film. To the lipid film was added a solution of PosPep (2 µg) in PBS (30 µL). The resulting mixture was vortexes, and allowed to hydrate for 10-30 min, followed by brief gentle vortexing and bath sonication (5 sec).

58. Preparation of DOTAP-Cl/Cholesterol/IgG F(ab) Fragment: DOTAP-Cl (10 µg, 0.2 µg/µL in chloroform, Avanti Polar Lipids, Inc) and Cholesterol (2.5 µg, 0.05 µg/µL in chloroform, Avanti Polar Lipids, Inc) was added to a micro centrifuge tube and air dried to produce a lipid film. To the lipid film was added a solution of FITC-IgG F(ab) fragment in PBS (30 µL). The resulting mixture was vortexes, and allowed to hydrate for 10-30 min, followed by brief gentle vortexing and bath sonication (5 sec).

59. Preparation of DOTAP-Cl/Cholesterol/IgG: DOTAP-Cl (10 µg, 0.2 µg/µL in chloroform, Avanti Polar Lipids, Inc) and Cholesterol (2.5 µg, 0.05 µg/µL in chloroform, Avanti Polar Lipids, Inc) was added to a micro centrifuge tube and air dried to produce a lipid film. To the lipid film was added a solution of cy3-IgG in PBS (30 μL). The resulting mixture was vortexes, and allowed to hydrate for 10-30 min, followed by brief gentle vortexing and bath sonication (5 sec).

Unless otherwise stated, dried polypeptide formulations were hydrated by addition of 30-50 μl PBS. Formulations were incubated at RT for 20 min at RT with occasional gentle vortexing and 5-10 sec bath sonication.

Example 5

Cell Growth

HeLa cells were maintained in DMEM containing 10% fetal bovine serum. For polypeptide delivery, cells were plated in 6-well plates containing glass cover slips at a density of 50,000-100,000 cells per well and grown for 24-48 hours before incubation with polypeptide formulations.

Example 6

Peptide Delivery to Cells

Two different techniques were used for contacting polypeptide formulations with cells. In both techniques, cells were grown to 30-70% confluency and washed once with 2 ml 37° C. PBS prior to addition of polypeptide formulations.

Technique #1: Peptide formulations were diluted by addition of 150 μl 37° C. PBS (180-200 μl total volume). Formulations were than added to cells on cover slips. Following a 5 min incubation at room temperature (RT) 0.8 ml 37° C. DMEM was added to each well and cells were again incubated for 5 min at RT. Media was then aspirated off cells and 2.0 ml DMEM containing 10% bovine serum was added. Cells were than incubated 40-60 min at 37° C. in a humidified $CO_2$ incubator.

Technique #2: Peptide formulations were diluted by addition of 950 μl 37° C. OptiMEM (GIBCO). Formulations were then added to cells on cover slips and incubated for 4 h at 37° C. in a humidified $CO_2$ incubator.

Visualization of polypeptide delivery to cells: In order to visually analyze polypeptide delivery, cells were washed 3× with PBS, fixed for 30 min at 4° C. in PBS containing 4% formaldehyde and washed 3× with PBS. Cover slips were then mounted onto slides for fluorescence microscopy using a Zeiss LSM510 laser confocal microscope. Rhodamine was detected by exciting with a HeNe laser at 543 nm and detecting with a 560 nm long pass filter. For control samples, peptides alone were used under the same concentrations.

Example 7

Demonstration of Peptide Delivery

Typically, for introduction of DNA into cells, a cationic lipid along with the helper lipid DOPE is used. The inclusion of DOPE is believed to facilitate exit of the complex from cellular endosomes. Similar strategies have also been employed in attempts to deliver proteins into cells, ie. cationic lipids with DOPE. We were unable to observe cytoplasmic delivery of polypeptides into cells with a number of liposomes when using typical formulations: formation of liposomes (cationic lipid/DOPE at 2:1 molar ratio) in the presence of the polypeptide, dilution of the liposomes in culture media and incubation of the liposomes with cells for several hours.

However, using our polypeptide modifications, formulations and cell incubation techniques, we have successfully delivered polypeptides to the cell interior, for examples see FIG. 1. The diffuse cellular staining patterns demonstrate that the polypeptides are cytoplasmically delivered. Endocytosis and then entrapment within endosomes would have appeared as a punctate staining pattern.

While the cationic lipid DOTAP was used in these examples, the modifications, formulations, and techniques used here would also be applicable to other cationic lipids.

Example 8

Demonstration of Protein Delivery

Figure 2:
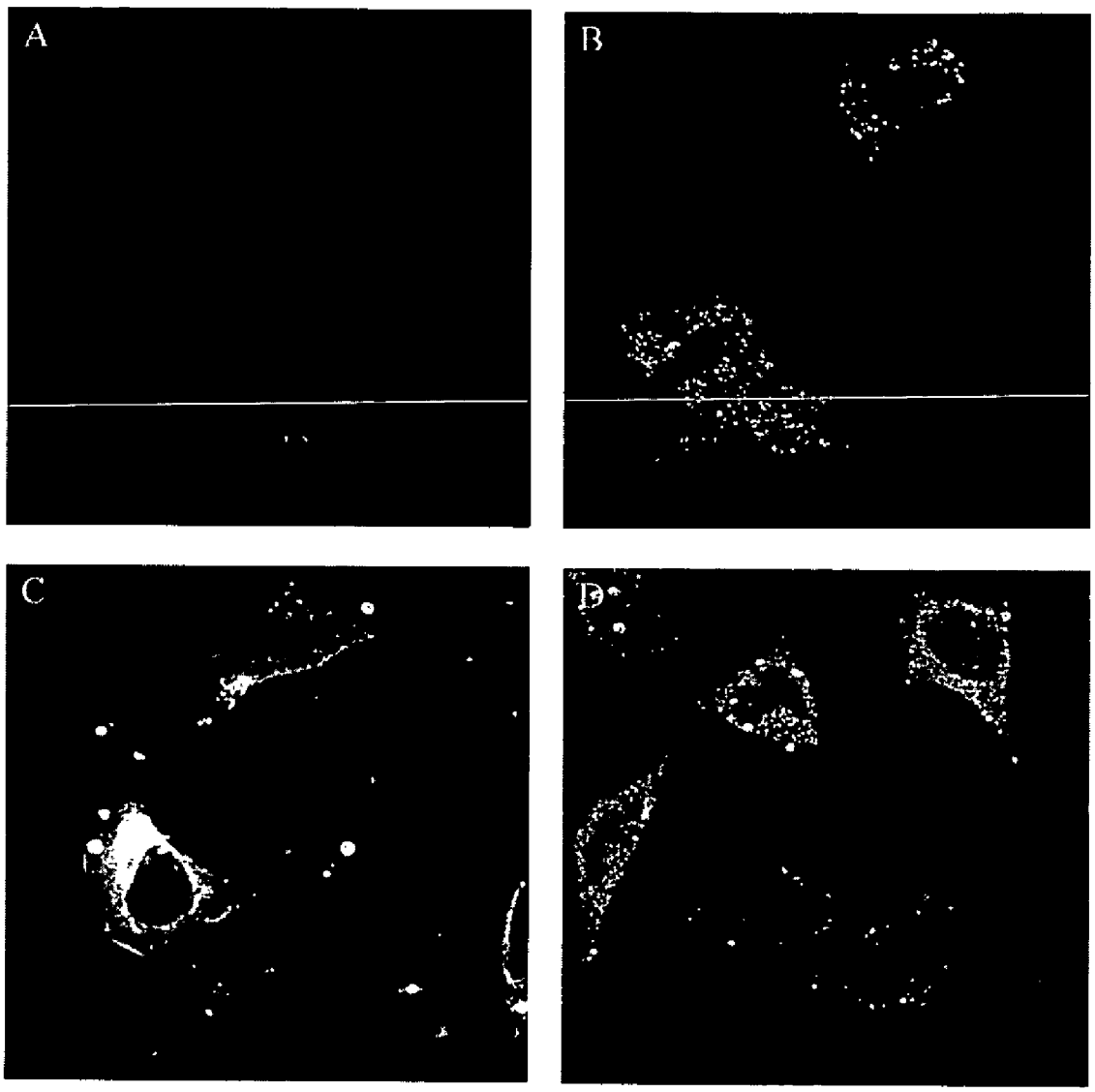
FIG. 2. Protein delivery to mammalian cells. (A) FITC-labeled BSA control, FITC-labeled BSA incubated with HeLa cells according to technique #2. (B) Modification # 26, technique #2. (C) Formulation #58, Technique #1. (D) Formulation #59, Technique #1. Formulations are described in example 4, techniques are described in example 6.

There is no receptor-specific or nonspecific interaction between Bovine Serum Albumin (BSA) and most cell types. Therefore, incubation of BSA with cells does not lead to cell association or internalization of the protein (see FIG. 2A). Similarly, there is also no association of most cell types with IgG's or IgG F(ab) fragments (data not shown). However, using the methods detailed above, we have successfully delivered all three of these proteins to HeLa cells. FIG. 2B shows the uptake of BSA when the BSA is modified according to modification method #26. Both IgG F(ab) fragment and IgG were delivered to HeLa cells using formulations #58 and #59 (FIGS. 2, C and D). These modifications and formulations could be used to deliver many different proteins to cells.

We claim:

1. A composition for intracellular delivery of a polypeptide, comprising: the polypeptide reversibly modified by reaction with an amphipathic 2-propionic acid-3-methyl maleic anhydride derivative having the general structure:

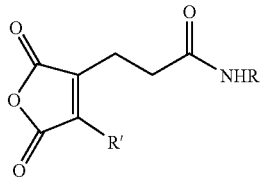

wherein R' is selected from the group consisting of hydrogen, alkyl group, and aryl group, and R is selected from the group consisting of alkyl group, aryl group, and aralkyl group wherein modification increases hydrophobicity of the polypeptide.

2. The composition of claim 1 wherein the polypeptide is further modified by reaction with a) an amphipathic 2-propionic acid-3-methyl maleic anhydride derivative having the general structure:

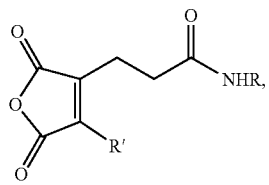

wherein R' is selected from the group consisting of hydrogen, alkyl group, and aryl group, and R consists of a functional group selected from the group consisting of: membrane active compounds, cell penetrating compounds, cell targeting signals, interaction modifiers, and steric stabilizers, or b) an alkyl chlorosilane having the general structure:

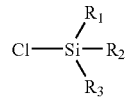

wherein $R_1$, $R_2$, and $R_3$ are independently selected from the group consisting of halogen, aryl group, alkyl group, and a functional group selected from the group consisting of: membrane active compounds, cell penetrating compounds, cell targeting signals, interaction modifiers, and steric stabilizers, and at least one of $R_1$, $R_2$, or $R_3$ is a functional group.

3. The composition of claim 1 wherein the composition is dehydrated.

4. The composition of claim 1 wherein the composition is associated with one or more lipids.

5. The composition of claim 4 wherein the lipids form a liposome.

6. The composition of claim 4 wherein the composition additionally contains a functional group selected from the list consisting of: membrane active compounds, cell penetrating compounds, cell targeting signals, interaction modifiers, steric stabilizers.

7. A process for delivering a polypeptide into a mammalian cell in vitro comprising:

a) forming a hydrophobized polypeptide by reacting the polypeptide with an amphipathic 2-propionic acid-3-methyl maleic anhydride having the general structure:

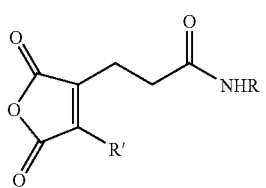
wherein R' is selected from the group consisting of hydrogen, alkyl group, and aryl group, and R is selected from the group consisting of alkyl group, aryl group, and aralkyl group; and,
b) contacting the cell with the polypeptide.
* * * * *

SEQUENCE LISTING

<160> NUMBER OF SEQ ID NOS: 3

<210> SEQ ID NO 1
<211> LENGTH: 13
<212> TYPE: PRT
<213> ORGANISM: Artificial
<220> FEATURE:
<223> OTHER INFORMATION: synthetic peptide derived from HIV REV nuclear
      export signal

<400> SEQUENCE: 1

Arg Leu Gln Leu Pro Pro Leu Glu Arg Leu Thr Leu Asp
1               5                   10

```
<210> SEQ ID NO 2
<211> LENGTH: 14
<212> TYPE: PRT
<213> ORGANISM: Artificial
<220> FEATURE:
<223> OTHER INFORMATION: synthetic positively charged peptide

<400> SEQUENCE: 2

Gly Lys Asn Arg Gly Lys Ser Ala Gln Ala Lys Arg Leu Arg
1               5                   10

<210> SEQ ID NO 3
<211> LENGTH: 12
<212> TYPE: PRT
<213> ORGANISM: Artificial
<220> FEATURE:
<223> OTHER INFORMATION: synthetic peptide derived from alpha tubulin
      gene

<400> SEQUENCE: 3

Gly Glu Gly Met Glu Glu Gly Glu Phe Ser Glu Ala
1               5                   10
```